(12) United States Patent
Jungbauer et al.

(10) Patent No.: US 11,963,303 B2
(45) Date of Patent: Apr. 16, 2024

(54) ELECTRONIC DEVICE FOR AN ENDOSCOPE, AND ENDOSCOPE

(71) Applicant: OLYMPUS WINTER & IBE GMBH, Hamburg (DE)

(72) Inventors: Sebastian Jungbauer, Hamburg (DE); Sven Pabst, Giekau (DE); Martin Wieters, Barsbuettel (DE)

(73) Assignee: OLYMPUS WINTER & IBE GMBH, Hambug (DE)

( * ) Notice: Subject to any disclaimer, the term of this patent is extended or adjusted under 35 U.S.C. 154(b) by 458 days.

(21) Appl. No.: 17/398,068

(22) Filed: Aug. 10, 2021

(65) Prior Publication Data
US 2022/0015239 A1    Jan. 13, 2022

Related U.S. Application Data

(63) Continuation of application No. PCT/EP2020/052732, filed on Feb. 4, 2020.

(30) Foreign Application Priority Data

Feb. 11, 2019  (DE) .......................... 102019103288.1

(51) Int. Cl.
*H05K 1/18*   (2006.01)
*A61B 1/00*   (2006.01)

(52) U.S. Cl.
CPC ......... *H05K 1/189* (2013.01); *A61B 1/00064* (2013.01); *A61B 1/00114* (2013.01); *H05K 2201/10121* (2013.01)

(58) Field of Classification Search
CPC ..................... H05K 1/18; H05K 1/189; H05K 2201/10121; A61B 1/00064; A61B 1/00114

(Continued)

(56) References Cited

U.S. PATENT DOCUMENTS

| 10,610,090 B2 | 4/2020 | Motohara et al. |
| 2010/0140730 A1 | 6/2010 | Soloviev et al. |

(Continued)

FOREIGN PATENT DOCUMENTS

| DE | 3616773 A1 | 11/1987 |
| DE | 102009044199 A1 | 6/2010 |

(Continued)

OTHER PUBLICATIONS

International Search Report dated Jul. 10, 2020 issued in PCT/EP2020/052732.

*Primary Examiner* — Tremesha S Willis
(74) *Attorney, Agent, or Firm* — Scully, Scott, Murphy & Presser, P.C.

(57) ABSTRACT

An electronic device including: a multilayer printed circuit board; and a molded retaining body; wherein the printed circuit board is formed of structured layers of conducting and non-conducting materials adhered together, the conducting materials form conductor tracks and contact areas, the printed circuit board being stiffened in a rigid region by stiffening material, the rigid region having electronic components and encapsulated in an epoxy; the printed circuit board having a flexible region that is more flexible than the rigid region, the flexible region having contact areas; the retaining body having an arc-shape formed on a radial inner side of the retaining body for arrangement on an inner tube of an endoscope; the retaining body having, on a radial outer side, a receiving contour for receiving and shaping the printed circuit board; and the retaining body having a retainer for holding the printed circuit board in a bent state.

20 Claims, 2 Drawing Sheets

(58) Field of Classification Search
USPC .......................................................... 174/31.5
See application file for complete search history.

(56) References Cited

U.S. PATENT DOCUMENTS

| | | |
|---|---|---|
| 2016/0273751 A1 | 9/2016 | Xiao et al. |
| 2017/0215718 A1 | 8/2017 | Schan et al. |
| 2019/0038117 A1 | 2/2019 | Motohara et al. |

FOREIGN PATENT DOCUMENTS

| | | |
|---|---|---|
| DE | 102016001048 A1 | 8/2017 |
| DE | 102017101932 B3 | 6/2018 |
| JP | H03-18343 A | 1/1991 |
| JP | 2016-533199 A | 10/2016 |
| WO | 2015/002847 A2 | 1/2015 |
| WO | 2017/040692 A1 | 3/2017 |
| WO | 2017/195605 A1 | 11/2017 |

ELECTRONIC DEVICE FOR AN ENDOSCOPE, AND ENDOSCOPE

CROSS-REFERENCE TO RELATED APPLICATION

The present application is a continuation of PCT/EP2020/052732 filed on Feb. 4, 2020, which is based upon and claims the benefit to DE 10 2019 103 288.1 filed on Feb. 11, 2019, the entire contents of each of which are incorporated herein by reference.

BACKGROUND

Field

The present disclosure relates to endoscopes and more particularly to an electronic device for an endoscope and to a corresponding endoscope comprising the electronic device.

Prior Art

Surgical endoscopes, such as video endoscopes, are autoclaved, i.e. cleaned and sterilized, in autoclaves after use. This is done using hot water and rinsing fluid, or hot steam and a positive or negative pressure. This means that the optical and electronic systems of the endoscope are also subjected to high temperatures and moisture, from which they must be protected in order to remain functional even under positive and negative pressure after frequently repeated use and cleaning.

Some of the electronics in an endoscope are therefore housed in hermetically sealed parts of the endoscope, such that this subset of the electronics, together with some of the optics and mechanics of an endoscope, is protected from the ingress of moisture. However, other parts of the endoscope, such as parts of the handle on the proximal end of the endoscope, are so-called "non-hermetic spaces" into which moisture can penetrate during autoclaving. If electronics are to be installed in the non-hermetic space of the endoscope, they must be protected accordingly against the effects of the cleaning and sterilization.

In the endoscopes sold by the applicant, the electronics arranged in the non-hermetic space are based on rigid FR4 printed circuit boards (PCB). The electronic components installed thereon are provided with a sheet metal housing which is filled with a silicone material in order to protect the circuit from moisture. The potting process is very time-consuming in this case. Furthermore, the metal housing is not electrically insulating. On account of the configuration of the housing, a large amount of installation space is used, and this would have to be even larger with an insulating housing material, since PEEK, for example, which would be considered for the housing material, cannot be produced with walls as thin as with steel.

In addition, in some endoscopes, a heating foil is installed in the form of an electrical printed circuit board, which, however, does not contain any electronic components or circuits that are sensitive to moisture except for the thermistor, and therefore only the thermistor is protected from moisture with a drop of adhesive even though the heating foil is not arranged in the hermetically sealed space. The same applies to a PCB used for the control buttons on the endoscope handle. Here, only three mechanical switching elements are integrated, and these do not need to be specially protected from moisture. However, it is also known that this PCB cannot withstand moisture forever, and therefore it must be preventively replaced during each servicing session. Both the heating foil and the control board are directly connected to cables.

Since the hermetic space in endoscopes is spatially limited, only small electronic circuits can be installed therein. Furthermore, it is not always possible to increase the size of the hermetic space in order to house additional electronics in the hermetic space. In any case, it is very laborious and increases susceptibility to errors on account of the larger number of hermetically sealed connections that are required.

If it becomes necessary to integrate additional electronic circuits in an endoscope, they must be placed in a non-hermetically sealed space and protected against the influence of moisture. However, installation space is also very limited in the non-hermetic space if the endoscope dimensions are not to be increased, and therefore only special solutions are possible for this.

SUMMARY

An object is to incorporate additional electronics into the non-hermetic space in an efficient manner.

Such object can be achieved by an electronic device for an endoscope, comprising an autoclavable flexi-rigid multilayer printed circuit board and a molded retaining body, wherein the printed circuit board is formed of structured layers of conducting and nonconducting materials that are adhered to one another, in which the conducting structures form conductor tracks and contact areas, is stiffened in a rigid region by an additional stiffening, is populated with electronic components and is encapsulated in an epoxy resin, and is configured to be flexible in a flexible region, which has contact areas, wherein the molded retaining body has, in cross-section, a basic arc-shaped form, which is formed on the radial inner side thereof for arrangement on an inner tube of an endoscope, which can be cylindrical, and on the radial outer side thereof has a receiving contour for receiving and shaping the flexi-rigid printed circuit board and a retainer for holding the printed circuit board in a bent state.

The electronic device comprising the autoclavable flexi-rigid multilayer printed circuit board and the molded retaining body can provide a suitable frame for introducing additional electronics into the non-hermetic space. This space can be a hollow-cylindrical space provided in the handle for integrating the printed circuit board and the electronic components arranged thereon. In order to fully utilize this space, the printed circuit board must be bent. A flexi-rigid printed circuit board can be used, since the electronic components have to be arranged on a rigid region of the printed circuit board. However, in order for it to be bent, the printed circuit board must also be flexible at least in part. In order to combine these two required properties, a flexi-rigid printed circuit board is used. As such, the printed circuit board can be laid around the inner cylinder or an inner tube of the endoscope that is spaced apart from the outer tube of the endoscope.

In order to increase installation security, a molded retaining body can be used for the printed circuit board. This makes handling particularly simple, since the printed circuit board can be formed into the required shape by the molded retaining body outside the endoscope such that it can be introduced into the hollow-cylindrical cavity in the non-hermetic space of the endoscope. The molded retaining body can be configured such that it receives the printed circuit board in a sealed state produced by providing the printed circuit board with a covering such that it is autoclavable.

In order to facilitate installation on the inner cylinder or rather inner tube of the endoscope, in one embodiment, the molded retaining body can be, in its basic arc-shaped form, formed along an arc of more than 180° and configured to be elastically resilient, wherein, the molded retaining body can be held in position on the inner tube by a press fit when it is placed on the inner tube of the endoscope. This makes it possible to avoid the situation in which installation in the axial direction is difficult, such as when the printed circuit board is installed with the molded retaining body in a tapered region of the inner cylinder or inner tube. Since the basic arc-shaped form follows the arc for more than 180°, the molded retaining body can be open on one side, such that it can be installed from the side. The molded retaining body can be pushed onto the inner cylinder by its opening. Since the shape is less than half open, the holder snaps onto the inner cylinder. At the same time, after the molded retaining body has been positioned, the inner cylinder can be surrounded to such an extent that it cannot fall off again. This can be assisted by the elasticity of the molded retaining body, which makes installation from the side possible and ensures that the molded retaining body is held in position on the inner cylinder or inner tube by clamping or a press fit.

Such configuration offers several advantages over the use of a shrink-on tube for insulation. There are instances where the taper of the inner cylinder of the endoscope is so great that a shrink-on tube does not has enough shrinking capacity to shrink onto the taper once installed past the wider regions. In cases such as these, a shrink-on tube is therefore not practicable. Another disadvantage of shrink-on tubes is that water can be drawn in under a shrink-on tube by capillary action, and therefore corrosion can occur on the metal inner cylinder underneath the shrink-on tube. However, since the molded retaining body does not sit on quite as completely as a shrink-on tube, this effect does not occur. This is due to the surface roughness of the molded retaining body and the fact that no close fit is produced with the inner cylinder or inner tube of the endoscope.

In embodiments, the molded retaining body can be made of an electrically insulating material, such as PEEK.

In order to hold the flexi-rigid printed circuit board, in embodiments, the receiving contour of the molded retaining body for receiving and shaping the flexi-rigid printed circuit board can have a fit for guiding the flexi-rigid printed circuit board in the direction of an endoscope axis and a fit for guiding the flexi-rigid printed circuit board perpendicularly to the endoscope axis. The endoscope axis should be understood to mean the longitudinal axis of the endoscope. Fits can be understood to mean contour elements that rise from the base surface of the molded retaining body as protuberances and that are configured in portions as the negative of parts of the shape of the printed circuit board, such it can be fitted in here. The protuberances or fit can prevent the printed circuit board from changing position.

In embodiments, the molded retaining body can comprise a slot-shaped receiver as a retainer for receiving and securing an end region of the flexible region of the flexi-rigid printed circuit board, wherein the slot-shaped receiver can be asymmetrical with respect to the fit in the direction of the endoscope axis. The slot-shaped receiver can be used to radially secure the flexible part of the printed circuit board and thus to prevent it from deviating from its position on the molded retaining body. The slot-shaped receiver can additionally form a fit that acts as a guide in the direction of the endoscope axis. The slot can be parallel to the corresponding first fit in the direction of the endoscope axis. The asymmetrical arrangement of the slot with respect to the fit in the direction of the endoscope axis means that the slot is axially shifted with respect to the first fit. This ensures that the printed circuit board cannot be rotated out of position or placed in the wrong orientation against the molded retaining body.

In other embodiments, the molded retaining body can comprise cut-outs and/or feedthroughs for cable ties, such that parts of the printed circuit board and/or cables can be fastened to the molded retaining body by cable ties. For example, temperature-resistant cable ties, for example made of PEEK, are suitable for securing the printed circuit board on the molded retaining body.

In embodiments, the molded retaining body can comprise multiple, such as three, flat portions for radially positioning the flexi-rigid printed circuit board, wherein the flexi-rigid printed circuit board can be configured to have target bending points that come to lie at the transitions between the flat portions of the molded retaining body when the flexi-rigid printed circuit board has been fitted. One of the flat portions can be intended for the rigid region of the printed circuit board and a second flat portion as well as, if applicable, a third flat region can be intended for the flexible part of the printed circuit board, such as in order to provide solder regions, for example for connection to cable ends or to other printed circuit boards. The flattened portions also reduce the bending stress on the printed circuit board such as on the mechanically loaded solder regions. The bending stress can be further reduced by the optionally provided target bending points.

In embodiments, the molded retaining body can comprise, on the radial outer side thereof, a receiving contour that can be oriented in parallel with a longitudinal axis of the endoscope for receiving another printed circuit board, such as a heater circuit board, which can be connected to the flexi-rigid printed circuit board. As such, the flexi-rigid printed circuit board and the other printed circuit board oriented in the direction of the longitudinal axis of the endoscope intersect. The point of intersection is well suited for directly interconnecting the two printed circuit boards, for example by one or more solder connections. For this purpose, the flexi-rigid printed circuit board can also comprise a connection region for the other printed circuit board that contacts the electronic circuit on the inside, which can be arranged in the rigid region of the flexi-rigid printed circuit board. The internal contacting in the printed circuit board can be produced in an automated process such that no errors can occur when the connection is manually produced during installation. In embodiments, the other printed circuit board can also comprise metal contact areas for connection to the flexi-rigid printed circuit board, which is connected or can be connected to correspondingly arranged metal contact areas of the flexi-rigid printed circuit board via direct connections, such as solder connections, in a state in which the other printed circuit board is received in the receiving contour of the molded retaining body for receiving the other printed circuit board.

Such object can also be achieved by an electronic device for an endoscope, comprising an autoclavable flexi-rigid multilayer printed circuit board that is formed of structured layers of conducting and non-conducting materials that are adhered to one another, in which the conducting structures form conductor tracks and contact areas, is stiffened in a rigid region by an additional stiffening, is populated with electronic components and is encapsulated in an epoxy resin, and is configured to be flexible in a flexible region, which has contact areas, the flexi-rigid printed circuit board comprises a cut-out in the flexible region, the inner edge of which has a contour with resilient arms that project into the cut-out and at their ends comprise the metal contact areas for connection to one or to the other printed circuit board, and the cut-out can have a greater width than the other printed circuit board, with respect to a direction that extends transversely to an endoscope axis.

This embodiment is inventive in and of itself and can also be combined with the above-described retaining body, but it is not dependent on the retaining body. It can be used for the mechanically resistant connection of the flexi-rigid printed circuit board to the above-described other printed circuit board, for example a heater circuit board.

The features of this embodiment produce several technical effects and advantages. Firstly, the combination of the cut-out with the formation of resilient arms and the solder connections increases the mechanical resistance of the bond between the two printed circuit boards. Mechanical loads are absorbed by the bending of the resilient arms, while the solder connections are themselves mechanically loaded to a lesser extent and are thus more durable. Furthermore, the solder region between the two printed circuit boards is problematic with regard to moisture. If water creates a contact path between the solder points, this can cause the electronics on the printed circuit board to malfunction. A water bridge of this kind can be formed when the water is drawn up by capillary action between two parts of printed circuit boards lying one on top of the other and collects there. Such a site of capillary action must be reliably sealed as a non-trivial measure. In so doing, it helps to provide a cut-out in the region in which the two printed circuit boards intersect. The resilient arms ensure that only very small transition regions remain and, accordingly, that little moisture can penetrate into these regions.

If the cut-out is wider than the width of the other PCBs, the overlap between adjacent solder connections can be eliminated. On account of the cut-out, the solder connections, including the soldering, can be easily protected by potting. It is thus possible to provide the connection between the two printed circuit boards with a coating that also makes these resistant to moisture. In embodiments, the connections, such as solder connections, between the flexi-rigid printed circuit board and the other printed circuit board are potted, such as with silicone. Furthermore, for the connection, the thin arms may be cut off in the free region next to the other printed circuit board and then unsoldered individually.

In embodiments, the soldering region for the cable may only be present and/or gold-plated on one side of the flexi-rigid printed circuit board. In embodiments, the soldering region for the other heating plate is gold-plated on both sides of the printed circuit board. This improves the solderability between the two printed circuit boards. Solder can therefore flow between both parts and create a better connection. In addition, this provides protection against skewed installation, since the soldering points for the cable would no longer be accessible if the printed circuit board were installed askew.

Such object can also be achieved by an endoscope having an above-described electronic device. Since the endoscope comprises a corresponding electronic device, it has the same features, properties and advantages as the above-described electronic device.

BRIEF DESCRIPTION OF THE DRAWINGS

Further features will become apparent from the description of embodiments together with the claims and the attached drawings. Embodiments can fulfill individual features or a combination of several features.

The embodiments are described below, without restricting the general idea of the invention, based on exemplary embodiments in reference to the drawings, whereby we expressly refer to the drawings with regard to all details that are not explained in greater detail in the text. In the figures.

In the drawings, the same or similar elements and/or parts are provided with the same reference numbers in each case; a reintroduction will therefore always be omitted.

DETAILED DESCRIPTION

Figure 1:
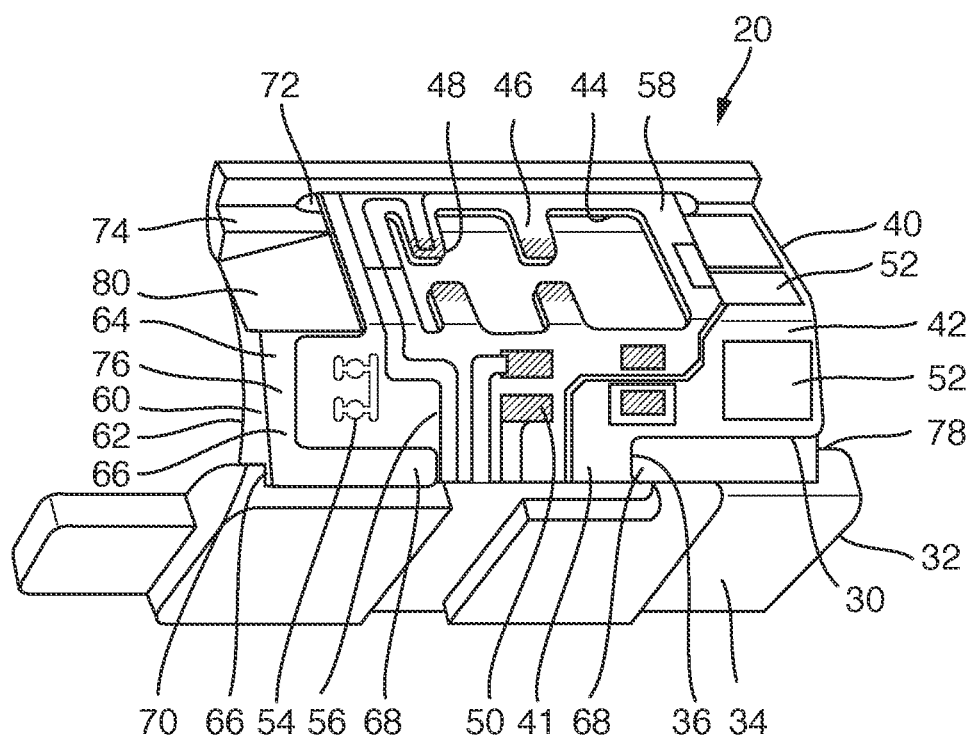
FIG. 1 illustrates a schematic perspective representation of an electronic device.

FIG. 1 is a schematic perspective representation of an electronic device 20 that comprises a flexi-rigid printed circuit board 30 and a molded retaining body 60 on which the flexi-rigid printed circuit board 30 is arranged and held. The molded retaining body 60 is an elongate base body having a basic arc-shaped form that is adapted, on the inner side 62 thereof, to the radius of an inner cylinder or inner tube of an endoscope and, to one side, comprises an opening by which it can be placed on the inner cylinder or inner tube. The retaining body 60 is manufactured from an elastic and electrically insulating material, for example a plastics material such as PEEK, such that it can snap onto a cylindrical body such as the inner cylinder of an endoscope. The opening is less than half the circumference of the circle.

The molded retaining body 60 is used to receive autoclavable electronics in the form of a flexi-rigid printed circuit board 30. Said printed circuit board comprises a rigid region 32, which is completely enclosed in an epoxy resin covering 34. Said rigid region is populated with electronic components 35, which are surrounded by a homogeneous coating of the epoxy resin covering 34 and are therefore protected against the effects of moisture during autoclaving of an endoscope. In order to be able to introduce the printed circuit board 30 in the hollow-cylindrical cavity of an endoscope in the region of the handle, the flexi-rigid printed circuit board 30 must be bent. For this purpose, the printed circuit board 30 comprises a flexible region 40, which leads into the rigid region 32 via a tapered feedthrough 36. The flexible region 40 of the printed circuit board 30 is not stiffened in the same way as the rigid region 32 and can therefore be bent into a suitable shape for insertion into the endoscope.

The flexible region 40 of the flexi-rigid printed circuit board 30 comprises target bending points 41, 42 at which the flexible region 40 can be bent such that flatter regions with contact points or metal contact areas 48, 50, 52 are created. These contact points or metal contact areas 48, 50, 52 serve various functions, for example electronic contacting or the establishment of connections to cables or other printed circuit boards. In the region more remote from the rigid region 32, the flexible region 40 comprises a cut-out 44, the inner contour of which comprises multiple arms 46, which are configured to be resilient and elastic on account of their material properties and the ends of which are provided in each case with metal contact areas 48. These are used to produce a solder connection with another printed circuit board. Additional metal contact areas 50, 52 are arranged so as to be distributed over the flexible region 40 of the printed circuit board 30.

Moreover, the flexible region 40 comprises LEDs 54, which may be used, for example, during the installation and manufacture of the electronics in order to check the functionality of the electronics on the flexi-rigid printed circuit board 30. Various conductor tracks 56 are also shown in FIG. 1 on the surface of the flexible region 40. Additional conductor tracks are embedded in layers of the multilayer flexible printed circuit board 30 and are therefore not visible in FIG. 1.

The outer side 64 of the molded retaining body 60 comprises a receiving contour 66, which is shaped such that the flexi-rigid printed circuit board 30 can be placed and held thereon or thereagainst. In order to secure the printed circuit board 30 in the axial direction and in the circumferential direction, the receiving contour 66 comprises, in the region of the tapered feedthrough 36 of the printed circuit board 30, an axial fit 68 and, on the side on the epoxy resin covering 34, a fit 70 in the circumferential direction, against or into which the corresponding part of the flexi-rigid printed circuit board can be placed. These are protuberances that adjoin edge contours of the printed circuit board 30. Furthermore, the molded retaining body 60 comprises a slot-shaped receiver 72 through which an end region 58 of the flexible region 40 of the flexi-rigid printed circuit board 30 is inserted and thus secured against lifting or twisting off. Further securing can be achieved using cable ties, for which the molded retaining body 60 comprises corresponding feedthrough openings, if applicable.

The molded retaining body 60 further comprises three flat portions 74, 76, 78 each adjoining different portions of the flexible region 40 of the printed circuit board 30 and, on the other side, adjoining a rigid region 32 of the flexi-rigid printed circuit board 30. The flat portion 74 of the molded retaining body 60 additionally comprises a receiving contour 80 for another printed circuit board, which extends in parallel with the longitudinal axis or longitudinal extension of the molded retaining body 60. The other printed circuit board may be a heating printed circuit board or heater circuit board. The corresponding heater circuit board is not shown in FIG. 1. Therefore, overall, the device 20 shown in FIG. 1 has a shape that is suitable for insertion of the autoclavable electronics in the non-hermetic space of an endoscope.

Figure 2:
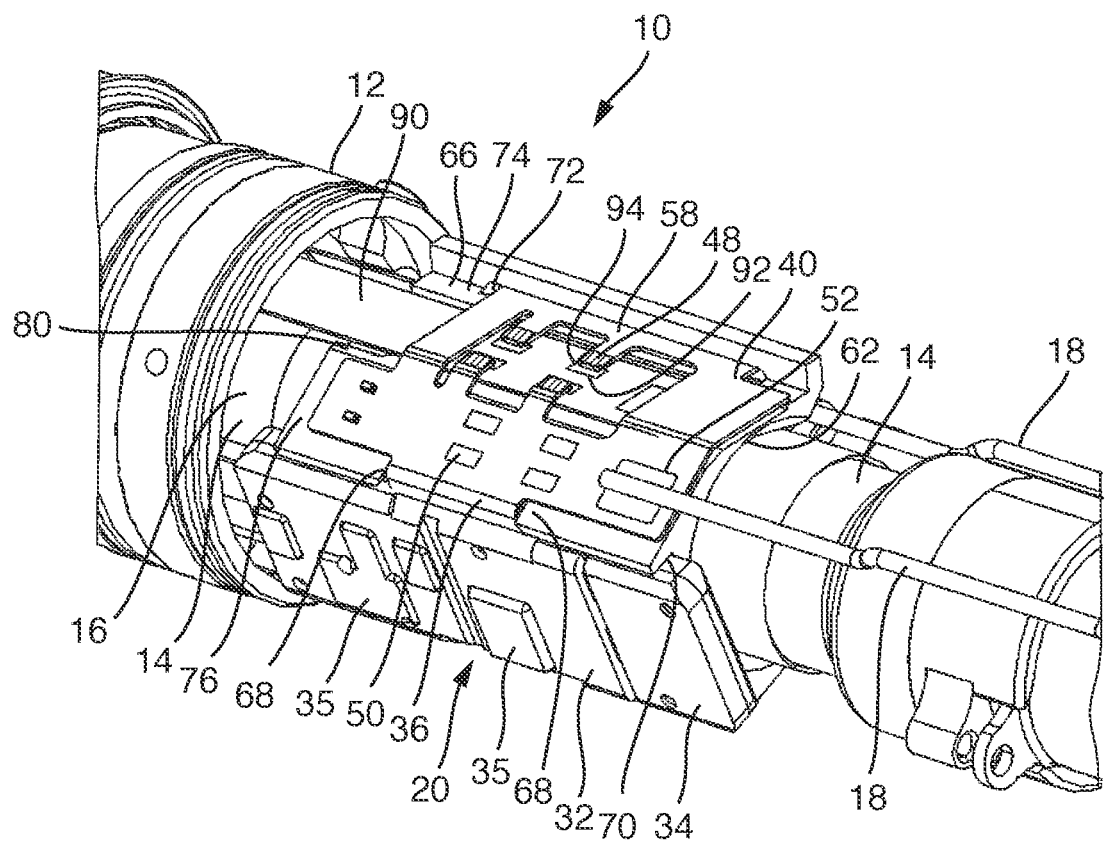
FIG. 2 illustrates a schematic perspective representation of part of an endoscope.

FIG. 2 is a schematic perspective representation of part of an endoscope 10. The device 20 presented in FIG. 1 is shown in conjunction with part of the endoscope 10 in the opened state. The handle 12 on the left-hand side of FIG. 2 comprises the cavity 16 around an inner tube 14 or inner cylinder in which the device 20 fits. As is clearly visible, the molded retaining body 60 is arranged with the inner side 62 thereof around the inner tube 14 of the endoscope 10, with an opening on the side of the drawing facing away from the viewer that allows the molded retaining body 60 to be pushed onto the inner tube 14 from the side. Cables 18 are also shown, one of which is connected to a metal contact area 52 in order to produce a mechanical connection by a solder connection. The individual strands in the cable are not shown. The metal contact areas 50 in the flexible region 40 of the flexi-rigid printed circuit board 30 are used to produce the electrical contacts with said strands not shown here. Another cable 18 extends along the inner tube 14 through the side opening of the molded retaining body 60 without contacting the autoclavable electronics of the device 20.

Furthermore, another printed circuit board 90 is shown, which extends proximally from the handle 12 along the longitudinal axis of the endoscope 10 and projects into the device 20. This other printed circuit board 90 is a heating printed circuit board, for example. It is received in the receiving contour 80 for the other printed circuit board 90 and extends in its receiving contour 80 between the molded retaining body 60 and the bottom side of the flexible region 40 of the flexi-rigid printed circuit board 30. In order to produce a mechanical and electronic connection, direct solder connections 94 are produced between the metal contact areas 48 on the ends of the arms 46 of the flexi-rigid printed circuit board 30 and corresponding contact areas 92 on the top side of the other printed circuit board 90.

These direct solder connections 94 hold the device 20 in the axial direction and thus additionally secure the device 20 on the inner tube 14 of the endoscope 10. In case of required maintenance or replacement work, the arms 46 can very easily be separated to release the connection. Alternatively, the solder connections 94 can be released by heating and melting the soldering tin.

Figure 3:
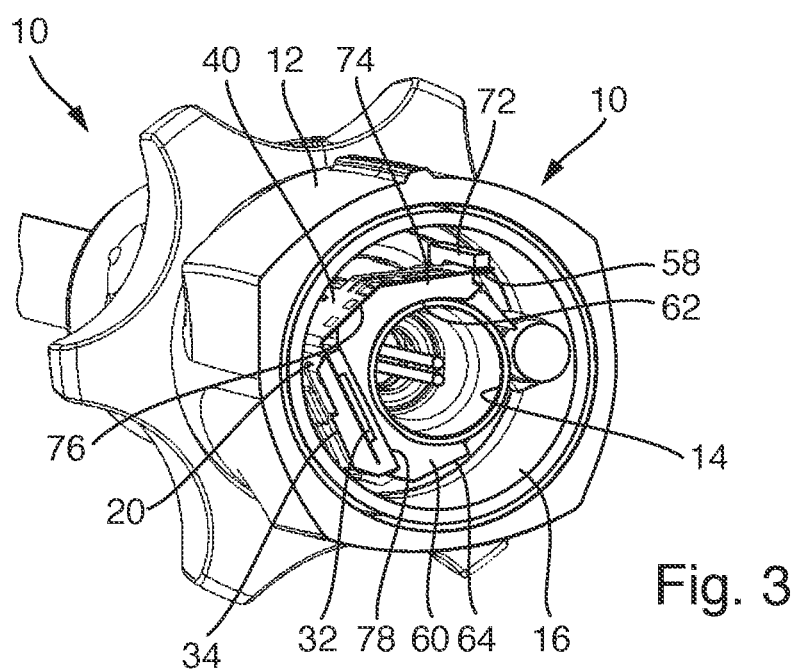
FIG. 3 illustrates is a schematic representation in cross-section of a proximal part of an endoscope.

FIG. 3 is a schematic representation in cross-section of a proximal part of an endoscope 10. The inner tube 14 and the molded retaining body 60, which is positioned with the inner side 62 thereof on the inner tube 14 and on which the flexi-rigid printed circuit board 30 is resting, can be seen clearly. The rigid region 32 with its epoxy resin covering 34 is resting on the flat portion 78 of the molded retaining body 60, while the flexible region 40 is resting on two other flat portions 74, 76, wherein the flat portion 74 is closed off by a molded part that forms a slot-shaped receiver 72 through which an end region 58 of the flexible region 40 of the printed circuit board 30 is guided.

The electronic components are protected from the effects of autoclaving by the epoxy resin covering 34. In order for, as far as possible, no moisture to be able to penetrate through the feedthrough by the flexible printed circuit board being guided out through the covering 34, and in order to protect the printed circuit board 30 in the flexible region 40 thereof as well, the transition in the region of the taper 36 as well as other parts of the flexible region 40 are also protected from moisture after the solder connections have been made, for example by a silicone coating. The coating can at least partially overlay the epoxy resin covering 34 of the rigid region 32, such that the electronic components 35 are protected against the ingress of moisture through the feedthrough in their covering 34.

While there has been shown and described what is considered to be particular embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

10 Endoscope
12 Handle
14 Inner tube
16 Cavity
18 Cable
20 Device
30 Flexi-rigid printed circuit board
32 Rigid region
34 Epoxy resin covering
35 Encapsulated electronic component
36 Tapered feedthrough
40 Flexible region
41, 42 Target bending point
44 Cut-out 46 Arm
48 Metal contact area
50 Metal contact area
52 Metal contact area
54 LED
56 Conductor track
58 End region of the flexible region of the printed circuit board
60 Molded retaining body
62 Inner side
64 Outer side
66 Receiving contour
68 Axial fit
70 Fit in the circumferential direction
72 Slot-shaped receiver
74 Flat portion
76 Flat portion
78 Flat portion
80 Receiving contour for other printed circuit board
90 Other printed circuit board
92 Metal contact area
94 Direct solder connection

What is claimed is:

1. An electronic device for an endoscope, the electronic device comprising:
an autoclavable flexi-rigid multilayer printed circuit board; and
a molded retaining body;
wherein the printed circuit board is formed of structured layers of conducting and non-conducting materials that are adhered to one another, in which the conducting materials form conductor tracks and contact areas,
the printed circuit board being stiffened in a rigid region by an additional stiffening material, the rigid region being populated with electronic components and encapsulated in an epoxy resin;
the printed circuit board having a flexible region configured to be more flexible than the rigid region, the flexible region having contact areas;
the molded retaining body having, in cross-section, an arc-shape formed on a radial inner side of the molded retaining body for arrangement on an inner tube of the endoscope;
the molded retaining body having, on a radial outer side of the molded retaining body, a receiving contour for receiving and shaping the flexi-rigid printed circuit board; and
the molded retaining body having a retainer for holding the printed circuit board in a bent state.

2. The electronic device according to claim 1, wherein the molded retaining body is formed along an arc of more than 180° and configured to be elastically resilient.

3. The electronic device according to claim 2, wherein the molded retaining body is held in position on the inner tube by a press fit when it is placed on the inner tube of the endoscope.

4. The electronic device according to claim 1, wherein the molded retaining body is formed of an electrically insulating material.

5. The electronic device according to claim 4, wherein the electrically insulating material is PEEK.

6. The electronic device according to claim 1, wherein the receiving contour has a first fit for guiding the flexi-rigid printed circuit board in a direction of an endoscope axis and a second fit for guiding the flexi-rigid printed circuit board perpendicularly to the endoscope axis.

7. The electronic device according to claim 6, wherein the molded retaining body comprises a slot-shaped receiver as a retainer for receiving and securing an end region of the flexible region of the flexi-rigid printed circuit board.

8. The electronic device according to claim 7, wherein the slot-shaped receiver is asymmetrical with respect to the first fit in the direction of the endoscope axis.

9. The electronic device according to claim 1, wherein the molded retaining body comprises one or more of cut-outs and feedthroughs for cable ties.

10. The electronic device according to claim 1, wherein the molded retaining body comprises multiple flat portions for radially positioning the flexi-rigid printed circuit board.

11. The electronic device according to claim 10, wherein the molded retaining body comprises three flat portions.

12. The electronic device according to claim 10, wherein the flexi-rigid printed circuit board is configured to have target bending points that lie at transitions between the flat portions of the molded retaining body when the flexi-rigid printed circuit board is fitted to the molded retaining body.

13. The electronic device according to claim 1, wherein the molded retaining body comprises, on the radial outer side, a receiving contour for receiving an other printed circuit board connected to the flexi-rigid printed circuit board.

14. The electronic device according to claim 13, wherein the receiving contour is oriented in parallel with a longitudinal axis of the endoscope.

15. The electronic device according to claim 13, wherein the other printed circuit board is a heater circuit board.

16. The electronic device according to claim 13, wherein the other printed circuit board comprises contact areas for connection to the flexi-rigid printed circuit board, which is connected to correspondingly arranged contact areas of the flexi-rigid printed circuit board via direct connections in a state in which the other printed circuit board is received in the receiving contour of the molded retaining body for receiving the other printed circuit board.

17. The electronic device according to claim 13, wherein the flexi-rigid printed circuit board comprises a cut-out in the flexible region, an inner edge of the cut-out having a contour with resilient arms that project into the cut-out and the ends of the resilient arms comprise the contact areas for connection to the other printed circuit board.

18. The electronic device according to claim 17, wherein the cut-out has a greater width than the other printed circuit board with respect to a direction that extends transversely to an endoscope axis.

19. The electronic device according to claim 16, wherein the connections between the flexi-rigid printed circuit board and the other printed circuit board are potted.

20. An endoscope comprising the electronic device according to claim 1.

* * * * *